United States Patent
Paszkowski et al.

(10) Patent No.: US 6,603,065 B2
(45) Date of Patent: *Aug. 5, 2003

(54) TRANSFORMATION OF HEREDITARY MATERIAL OF PLANTS

(75) Inventors: Jerzy Paszkowski, Zurich (CH); Ingo Potrykus, Magden (CH); Barbara Hohn, Bottmingen (CH); Raymond Douglas Shillito, Chapel Hill, NC (US); Thomas Hohn, Bottmingen (CH); Michael William Saul, Zurich (CH); Vaclav Mandak, Zunzgen (CH)

(73) Assignee: Syngenta Investment Corporation, Wilimington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/726,081

(22) Filed: Nov. 29, 2000

(65) Prior Publication Data

US 2001/0029619 A1 Oct. 11, 2001

Related U.S. Application Data

(62) Division of application No. 08/473,893, filed on Jun. 7, 1995, now Pat. No. 6,201,169, which is a continuation of application No. 08/038,778, filed on May 29, 1993, now Pat. No. 5,453,367, which is a continuation of application No. 07/485,790, filed on Feb. 23, 1990, now Pat. No. 5,231,019, which is a continuation-in-part of application No. 07/366,285, filed on Jun. 13, 1989, now abandoned, which is a continuation of application No. 07/157,115, filed on Feb. 10, 1988, now abandoned, which is a continuation of application No. 06/730,025, filed on May 3, 1985, now abandoned.

(30) Foreign Application Priority Data

| | | |
|---|---|---|
| May 11, 1984 | (CH) | 2336/84 |
| Feb. 11, 1985 | (CH) | 606/85 |
| Apr. 1, 1995 | (CH) | 1398/85 |

(51) Int. Cl.[7] ............... C12N 15/82; C12N 15/87; C12N 5/04; C12N 5/10; A01H 5/00
(52) U.S. Cl. ............... 800/306; 800/278; 800/288; 800/292; 435/419; 435/421; 435/468; 435/470
(58) Field of Search ............... 800/278, 288, 800/292, 306; 435/419, 421, 468, 470

(56) References Cited

U.S. PATENT DOCUMENTS

| | | | | |
|---|---|---|---|---|
| 4,394,448 A | 7/1983 | Szoka | | 435/172.3 |
| 4,407,956 A | 10/1983 | Howell | | 435/172.3 |
| 4,536,475 A | 8/1985 | Anderson | | 435/172.3 |
| 4,684,611 A | 8/1987 | Schilperoort et al. | | 435/172.3 |
| 5,034,322 A | 7/1991 | Rogers et al. | | 435/172.3 |
| 5,188,958 A | 2/1993 | Moloney et al. | | 435/419 |
| 5,231,019 A | 7/1993 | Paszkowski et al. | | 435/172.3 |
| 5,453,367 A | 9/1995 | Paszkowski et al. | | 435/172.3 |

FOREIGN PATENT DOCUMENTS

| | | |
|---|---|---|
| CA | 1208146 | 7/1986 |
| EP | 0086537 | 8/1983 |
| EP | 0114529 | 8/1984 |
| EP | 0122791 | 10/1984 |
| EP | 0140566 | 5/1985 |
| GB | 2140822 | 12/1984 |
| WO | WO 83/01176 | 4/1983 |
| WO | WO 842920 | 8/1984 |

OTHER PUBLICATIONS

Altherr et al., "Transformation and Storage of Competent Yeast Cells", *Genetic Engineering in Eukaryotes, Series A: Life Sciences*, 61: 33–52 (1983).

Bevan et al., "A Chimaeric antibiotic resistance gene as a selectable marker for plant cell transformatiom", *Nature*, 304: 184–187 (1983).

Case et al., "Transformation in Fungi", *Genetic Engineering in Eukaryotes, Series A: Life Sciences*, 61: 1–5 (1983).

Chilton, "A Vector for Introducing New Genes into Plants", *Scientific American*, 248: 50–59 (1983).

Cocking, "Use of Protoplasts for Plant Genetic Manipulations", *Plant Tissue Culture*, 501–503 (1982).

Cocking, "Plant Genetic Manipulations: Applications from Plant Somatic Cell Genetics", *Genetic Engineering in Eukaryotes, Series A: Life Sciences*, 61: 187–194 (1983).

Davely et al., "Transformation of Petunia Protoplasts by Isolated Agrobacterium Plasmids", *Plant Science Letters*, 18: 307–313 (1980).

Fernandez et al., "Incorporation and Maintenance of Recombinant–DNA Plasmid Vehicles pBR313 and pCR1 In Plant Protoplasts", *FEBS*, 87(2): 277–282 (1978).

Fischer et al., "Manipulation and expression of genes in Eukaryotes", Nagley et al., eds. Academic Press, 241–244 (1983).

Fraley et al., "Expression of bacterial genes in plant cells", *Proc. Natl. Acad. Sci.*, 80: 4803–4807 (1983).

Garapin et al., "DNA Transfer into Animal Cells", *Genetic Engineering in Eukaryotes, Series A: Life Sciences*, 61: 37–42 (1983).

Garapin et al., "The Dominant Selective Marker APH 3' and the Study of the Expression of the Cotransfected Gene", *Genetic Engineering in Eukaryotes, Series A: Life Sciences*, 61: 43–51 (1983).

Goodman et al., "Gene Transfer in Crop Improvement", *Science*, 236: 48–54 (1987).

Herrera–Estrella et al., "Expression of Chimaeric Genes Transferred into Plant Cells Using a Ti–Plasmid–Derived Vector", *Nature*, 303: 209–213 (1983).

(List continued on next page.)

Primary Examiner—David T. Fox
(74) Attorney, Agent, or Firm—Randee S. Schwartz

(57) ABSTRACT

A novel process for the direct transfer of foreign genes to plant genomes is described. The novel process comprises placing a gene under the control of plant expression signals and transferring it, by contact with protoplasts without the aid of natural systems for infecting plants, direct to plant cells from which genetically transformed plants can subsequently be derived.

10 Claims, 2 Drawing Sheets

OTHER PUBLICATIONS

Herrera–Estrella et al., "Chimeric Genes as Dominant Selectable Markers In Plant Cells", *EMBO J.*, 2(6): 987–995 (1983).

Hiatt et al., "Introduction and Expression in Plants of a Glyphosate Resistant aroA Gene Isolated From *Salmonella Typhimurium*", *FEBS*, 83:479–487 (1984).

Hinnen et al., "Transformation of Yeast", *Proc. Natl. Acad. Sci.*, 75(4): 1929–1933 (1978).

Hohn et al., "Drug Resistant Plant Cell Lines After Treatment of Protoplasts with Hybrid DNA", *J. Cellular Biochemistry*, Abstract: 268 (1983).

Horsch et al., "Inheritance of Functional Foreign Genes in Plants", *Science* 223: 496–498 (1984).

Hughes et al., "Fate of Bacterial Plasmid DNA During Uptake by Barley Protoplasts", *FABS Letters*, 79(1): 80–84 (1977).

Ito et al., "Transformation of Intact Yeast Cells Treated with Alkali Cations", *J. of Bacteriology*, 153: 163–168 (1983).

Jones et al., "Reproducible Regeneration of Callus from Suspension Culture Protoplasts of the Grass *Lolium Multiflorum*", *Z. Pflanzenphysiol.*, Bd. 105: 267–274 (1982).

Kao et al., *Planta*, "Plant Protoplast Fusion and Growth of Intergeneric Hybrid Cells*", 120: 215–227 (1974).

Kado et al., "Bacterial–Plant Gene Cloning Shuttle Vectors", *Genetic Engineering in Eukaryotes, Series A: Life Sciences*, 61: 103–110 (1983).

Kleinhofs et al., Nitrate Reductase Genes as Selectable Markers for Plant Cell Transformation:, *Genetic Engineering in Eukaryotes, Series A: Life Sciences*, 61: 215–231 (1983).

Korohoda et al., *Z. Pfanenphysiol.*, "High Efficiency Genetic Transformation in Maize Induced by Exogenous DNA", 94: 95–99 (1979).

Koziel et al., *J. Mol. Appl. Genet.*, "A Cauliflower Mosaic Virus Promoter Directs Expression of Kanamycin Resistance in Morphogenic Transformed Plant Cells", 2(6): 549–562 (1984).

Krens et al., "In Vitro Tranformation of Plant Protoplasts with Ti–Plasmid DNA", *Nature*, 296: 72–74 (1982).

Loerz et al., "Gene Transfer to Cereal Cells Mediated by Protoplast Transformation", *Mol. Gen. Genet.*, 199: 178–182 (1985).

Loerz et al., *Plant Tissue Culture*, "Transformation Studies Using Synthetic DNA Vectors Coding for Antibiotic Resistance", 511–512 (1982).

Lu et al., "Isolation and Culture of Protoplasts of *Panicum Maximum* Jacq. (Guinea Grass): Somatic Embryogenesis and Plantlet Formation", *Z. Pflanenphysiol.*, 104: 311–318 (1981).

Lurquin, "Genetic Engineering of Plant Cells: A Rapid Overview", *Genetic Engineering in Eukaryotes, Series A: Life Sciences*, 61: 99–110 (1983).

Muller–Neumann et al., *Mol. Gen. Genet.*, "The DNA sequence of the transposable element Ac of *Zea mays* L.", 198: 19–24 (1984).

Murai et al., "Phaseolin Gene From Bean is Expressed After Transfer to Sunflower Via Tumor–Inducing Plasmid Vectors", *Science*, 222: 476–482 (1983).

Neumann et al., "Gene Transfer into Mouse Lyoma Cells by Electroporation in High Electric Fields", *EMBO J.*, 7: 841–845 (1982).

Ohgawara et al., "Uptake of Liposome–Encapsulated Plasmid DNA by Plant Protoplasts . . . ", *Protoplasma*, 116: 145–148 (1983).

Ondrej, "Detection of Nopaline Dehydrogenase and Lysopine Dehydrogenase Activities in Crown Gall Tumors of Different Plant Species", *Biologia Planatarum*, 25(5): 378–384.

Paszkowski et al., "Direct Gene Transfer to Plants", *EMBO Journal*, 3(12): 2717–2722 (1984).

Pelham et al., "A Synthetic Heat–Shock Promoter Element Confers Heat–Inducibility On The Herpes Simplex Virus Thymidine Kinase Gene", *EMBO J.*, 1(11): 1473–1477 (1982).

Shillito et al., "Approaches to Plant Protoplast Transformation Using Drug Resistance and Auxotroph Complementation as Selective Markers", *Genetic Engineering in Eukaryotes, Series A: Life Sciences*, 61: 265–276 (1983).

Steinbiss et al., "Plant Protoplasts", *Int. Rev. Cytol.*, 16: 191–208, Academic Press Inc. (1983).

Mathews et al., "Regeneration of Shoots Form *Brassica Juncea* (LINN) Czern and Coss Cells Transformed by *Agrobacterium Tumefaciens* and Expression of Nopaline Dehydrogenase Genes", *Plant Science*, 39: 49–54 (1985).

Li et al., "Somatic Embryogenesis in Quite a Direct Way in Cultures of Mesophyll Protoplasts of *Brassica Napus* L.", *Plant Cell Reports*, 1: 209–211 (1982).

Pua et al., "Transgenic Plants of *Brassica Napus* L.", *Bio/Technology*, 5: 815–817 (1987).

Laser et al., "Transformation of Protoplasts from *Brassica Campestris* with *Agrobacterium Tumefaciens*", *Official Journal of the FESP*, 64(2): 67 (1985).

Zee et al., "Cole Crops", *Handbook of Plant Cell Culture*, vol. 3(IV), 227–246 (1986).

De Greve et al., "Regeneration of Normal And Fertile Plants That Express Octopine Synthase, From Tobacco Crown Galls After Deletion of Tumour–Controlling Functions", *Nature*, 300: 752–755 (1982).

Ohlsson et al., "Transformation of *Brassica Campestris* Protoplasts With *Agrobacterium Tumefaciens*", *Hereditas*, 108(2): 173–177 (1988).

Yadav et al., "Short Direct Repeats Flank the T–DNA On A Nopaline Ti Plasmid", *Proc. Natl. Acad. Sci. USA*, 79: 6322–6326 (1982).

Zambryski, P., "Basic Processes Underlying Agrobacterium–Mediated DNA Transfer to Plant Cells", *Ann. Rev. Genet.*, 22: 1–30 (1988).

Flavell et al., "Prospects For Transforming Monocot Crop Plants", *Nature*, 307: 108–109 (1984).

Potrykus, I., "Gene Transfer To Cereals: An Assessment", *Biotechnology*, 8(6): 535–542 (1990).

CONSTRUCTION OF THE PLASMIDS pCaMV6Km

TRANSFORMATION OF HEREDITARY MATERIAL OF PLANTS

CROSS REFERENCES TO RELATED APPLICATIONS

This application is a divisional of application Ser. No. 08/473,893, filed Jun. 7, 1995 and issued Mar. 13, 2001 as U.S. Pat. No. 6,201,169, which is incorporated herein by reference and which is a continuation of application Ser. No. 08/038,778, filed Mar. 29, 1993 and issued Sep. 26, 1995 as U.S. Pat. No. 5,453,367, which is a continuation of Ser. No. 07/485,790, filed Feb. 23, 1990 and issued Jul. 27, 1993 as U.S. Pat. No. 5,231,019, which is a continuation-in-part of abandoned application Ser. No. 07/366,285, filed Jun. 13, 1989, which is a continuation of abandoned application Ser. No. 07/157,115, filed Feb. 10, 1988, which is a continuation of abandoned application Ser. No. 06/730,025, filed May 3, 1985.

FIELD OF THE INVENTION

The present invention relates to a novel process for transforming hereditary material of plants and to the plant products obtained by said process.

Plants having novel and/or improved properties can be produced by introducing new genetic information into plant material.

BACKGROUND

In view of the rapid rise in world population and the concomitant increase in the need for food and raw materials, increasing the yield of useful plants as well as the increased extraction of plant storage substances, and in particular advances in the field of nutrition and medicine, are among the most urgent tasks of biological research. In this connection, the following essential aspects may be mentioned by way of example: strengthening the resistance of useful plants to unfavourable soil or climatic conditions as well as to disease and pests; increasing resistance to plant protective agents such as insecticides, herbicides, fungicides and bactericides; and a useful change in the nutrient content or of the harvest yield of plants. Such desirable effects could be produced generally by induction or increased formation of protective substances, valuable proteins or toxins. A corresponding influence on the hereditary material of plants can be brought about, for example, by inserting a specific foreign gene into plant cells without utilising conventional breeding methods.

The transfer of novel DNA sequences into plant cells using genetically manipulated plant infecting bacteria has been described in the literature in a number of publications, for example Nature, Vol. 303, 209–213 (1983); Nature, Vol. 304, 184–187 (1983); Scientific American 248(6), 50–59 (1983); EMBO-Journal 2(6), 987–995 (1983); Science 222, 476–482 (1983); Science 223, 247–248 (1984); or Proc. Natl. Acad. Sci. USA 80, 4803–4807 (1983). In these publications, the natural properties of these bacteria for infecting plants were utilised to insert new genetic material into plant cells. So far such insertion has been made using preferably *Agrobacterium tumefaciens* itself or the Ti plasmid thereof, and also cauliflower mosaic virus.

SUMMARY

In contradistinction thereto, the novel process of this invention makes possible the direct transfer of a gene without the use of biological vectors, in particular, without the T-DNA border regions of the Ti-plasmid. Pathogens have been used as vectors in the known processes. As the process of this invention is performed without pathogens, the limitations imposed by the host specificity of pathogens also do not apply. The development of the plants on which the novel process of transformation is carried out is not impaired by said process.

In addition to the process for transforming hereditary material of plants, the present invention also relates to the products obtainable by said process, in particular protoplasts and plant material derived therefrom, for example cells and tissues, in particular complete plants that have been regenerated from said protoplasts and the genetically identical progeny thereof.

DETAILED DESCRIPTION

Figure 1:
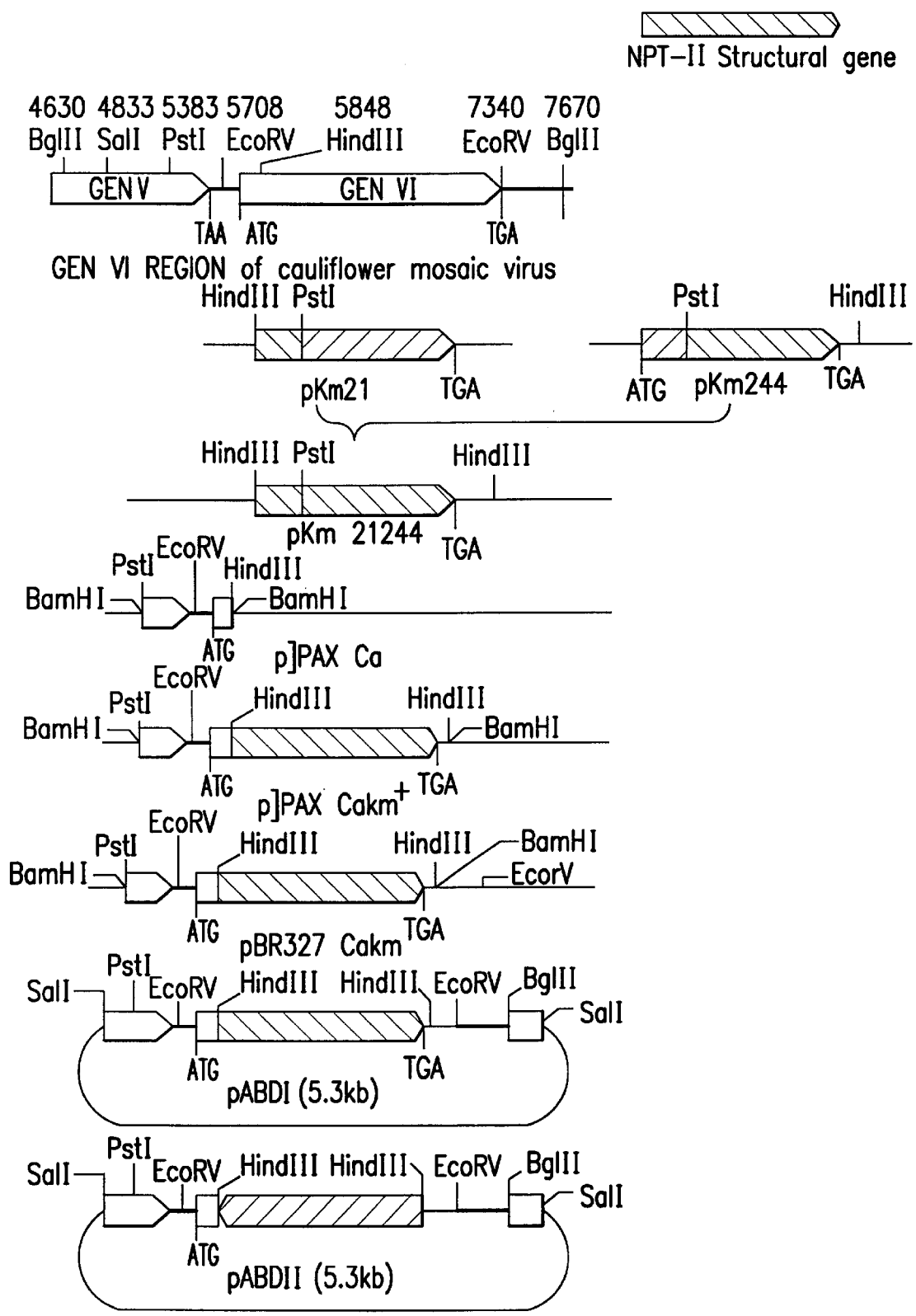
FIG. 1 depicts the construction of the pABDI and pABDII plasmids.

Within the scope of the present invention, the following definitions apply:

| | |
|---|---|
| gene: | structural gene with flanking expression signals |
| structural gene: | protein-coding DNA sequence |
| expression signals: | promoter signal and termination signal |
| plant expression signal: | expression signal that functions in plants |
| promoter signal: | signal that initiates transcription |
| termination signal: | signal that terminates transcription |
| enhancer signal: | signal that promotes transcription |
| replication signal: | signal that makes possible DNA replication |
| integration signal: | DNA sequence that promotes the integration of the gene into genomic DNA |
| hybrid gene: | gene constructed from heterologous DNA sequences, i.e. DNA sequences of different origin that may be natural as well as synthetic DNA sequences |
| carrier DNA: | a neutral (i.e. not participating in the function of the gene) DNA sequence flanking the gene |
| isolated gene: | DNA sequence coding for a single protein and separated from the original DNA |
| NPT II gene: | neomycin 3'-phosphotransferase gene, type II, of transposon Tn 5 [Rothstein, S. J. and W. S. Retznikoff, Cell 23, 191–199 (1981)] |
| genomic DNA: | DNA of the plant genome (total or part thereof). |

The present invention is concerned with a novel process for the transformation of hereditary material of plants, which process comprises transferring a gene direct into plant cells without the aid of natural systems for infecting plants. Such transformation is accordingly a vector-free transformation. In this vector-free transformation, the foreign gene for insertion is under the control of plant expression signals. The vector-free transformation of plant genes is preferably carried out by introducing a foreign gene for insertion into plant cells together with plant protoplasts acting as recipients (receptor protoplasts) into a suitable solution and leaving them until the gene has been taken up by the protoplasts.

As protoplasts it is preferred to use those of a single plant species or of a systematic unit which is a suborder of a species. The foreign gene and the protoplasts are conveniently left in the solution for a period of time ranging from several seconds to several hours, preferably from 10 to 60 minutes, most preferably for 30 minutes.

The process of this invention is susceptible of broad application. Thus it is possible to transfer any structural genes of plant origin, for example the zein gene [Weinand, U., et al., Mol. Gen. Genet. 182, 440–444 (1981)], of animal origin, for example the TPA gene [tissue-type plasminogen activator gene; Pennica, D., et al., Nature 301, 214–221 (1983)], of microbial origin, for example the NPT II gene, or also of synthetic origin, for example the insulin gene [Sepien, P., et al., Gene 24, 289–297 (1983)], into hereditary material of plants, provided that the structural genes are flanked by expression signals which are expressed in plants and which expression signals may be of plant, animal, microbial or synthetic origin.

The transferred genes, consisting of structural gene and flanking expression signals, may be naturally occurring genes as well as hybrid genes. In the process of this invention, it is preferred to use those genes whose expression signals are of animal or, in particular, of plant or synthetic origin. Exemplary of such genes are:

a) complete genes of plants consisting of the structural gene with its natural expression signals;
b) completely synthetic genes consisting of a structural gene of synthetic origin, flanked by expression signals of synthetic origin;
c) structural genes of plant origin, flanked by plant expression signals, with the structures and expression signals originating from various plant species;
d) structural genes of plant origin, flanked by expression signals of synthetic origin;
e) structural genes of animal, microbial or synthetic origin, flanked by expression signals of plant origin; or
f) structural genes of animal or microbial origin, flanked by expression signals of synthetic origin.

Most preferred are structural genes of bacterial origin, flanked by expression signals of plant origin, in particular those originating from plant viruses. Particularly suitable expression signals for use in the process of this invention are the expression signals of gene VI of cauliflower mosaic virus.

The hybrid genes are prepared by microbiological techniques which are known per se, retaining the reading frame of the coding for the proteins to be produced by the plant cell. Such techniques are known and are described e.g. in the following publications: "Molecular Cloning", Maniatis, T., Fritsch, E. F. and J. Sambrook, Cold Spring Harbor Laboratory, 1982, and "Recombinant DNA Techniques", Rodriguez, R. L. and R. C. Tait, Addison-Wesley Publishing Comp., London, Amsterdam, Don Mills. Ontario, Sydney, Tokyo, 1983.

To integrate the foreign gene into the genomic DNA of the plant cell, it is advantageous if the gene, consisting of structural gene and plant expression signals, is flanked by neutral DNA sequences carrier DNA). The carrier DNA may consist of two linear DNA strands, so that the construction to be inserted into the plant cell is a linear DNA molecule. The DNA sequence prepared for the gene transformation can, however, also have an annular structure (plasmid structure). Such plasmids consist of a DNA strand into which the foreign gene containing the expression signals is integrated. The carrier DNA can be of synthetic origin or can be obtained from naturally occurring DNA sequences by treatment with suitable restriction enzymes. Thus, for example, naturally occurring plasmids which have been opened with a selective restriction enzyme are suitable for use as carrier DNA.

Exemplary of such a plasmid is the readily obtainable pUC8 plasmid (described by Messing, J. and J. Vieira, Gene 19, 269–276, 1982). Fragments of naturally occurring plasmids can also be used as carrier DNA. For example, the deletion mutant for gene VI of cauliflower mosaic virus can be used as carrier DNA.

The probability of the genetic transformation of a plant cell can be enhanced by different factors. Accordingly, as is known from experiments with yeast, the number of successful stable gene transformations increases 1) with the increasing number of copies of the new genes per cell,
2) when a replication signal is combined with the new gene, and
3) when an integration signal is combined with the new gene.

The process of this invention is therefore susceptible of especially advantageous application when the transferred gene is combined with a replication signal which is effective in plant cells or with an integration signal which is effective in plant cells, or which is combined with both signals.

The expression of a gene in a plant cell depends on the transcription frequency of the gene in a messenger RNA sequence. It is therefore advantageous if the new gene is combined with an enhancer signal that promotes this transcription. Methods meriting particular attention are those for transferring a gene which is combined with replication, integration and enhancer signals that are effective in plants.

It is further of great technical advantage if the transferred gene has a selective marker function, i.e. if the transformed plant cells can be separated from the non-transformed plant cells under specific conditions of selection. A marker function of this kind permits the process to be carried out efficiently in that only those plant cells need to be regenerated to calli or complete plants by microbiological techniques, the hereditary material of which plants contains a gene capable of expression that permits marker-specific methods of selection.

Whereas protoplasts, cell culture cells, cells in plant tissues, pollen, pollen tubes, egg-cells, embryo-sacs or zygotes amd embryos in different stages of development are representative examples of plant cells which are suitable starting materials for a transformation, protoplasts are preferred on account of the possibility of using them direct without further pretreatments.

Isolated plant protoplasts, cells or tissues can be obtained by methods which are known per se or by methods analogous to known ones.

Isolated plant protoplasts which are also suitable starting materials for obtaining isolated cells and tissues can be obtained from any parts of the plant, for example from leaves, embryos, stems, blossoms, roots or pollen. It is preferred to use leaf protoplasts. The isolated protoplasts can also be obtained from cell cultures. Methods of isolating protoplasts are described e.g. in Gamborg, O. L. and Wetter, L. R., Plant Tissue Culture Methods, 1975, 11–21.

The transfer of the new genes into plant cells is effected direct without using a natural system for infecting plants such as a plant bacterium, a plant virus, or transfer by insects or phytopathogenic fungi. This is achieved by treating the plant cells which it is desired to transform direct with the gene to be transferred by introducing the foreign gene and plant protoplasts into a suitable solution and leaving them therein until the foreign gene has been taken up by the protoplasts. The transformation frequency can be increased by combining this step with techniques which are employed in microbiological research for gene transfer, for example by treatment with poly-L-ornithine or poly-L-lysine, liposome fusion, DNA protein complexing, altering the charge at the protoplast membrane, fusion with microbial protoplasts, or calcium phosphate co-precipitation and, in particular, by treatment with polyethylene glycol, heat shock and electroporation, as well as a combination of these last three mentioned techniques.

Suitable solutions into which the foreign gene and the receptor protoplasts are introduced are preferably the osmotically stabilised culture media employed for protoplast cultures.

Numerous culture media are already available which differ in their individual components or groups of components. However, the composition of all media is in accordance with the following principle: they contain a group of inorganic ions in the concentration range from about 10 mg/l to several hundred mg/l (so-called macroelements such as nitrate, phosphate, sulfate, potassium, magnesium, iron), a further group of inorganic ions in maximum concentrations of several mg/l (so-called microelements such as cobalt, zinc, copper, manganese), then a number of vitamins (for example inositol, folic acid, thiamine), a source of energy and carbon, for example saccharose or glucose, and also growth regulators in the form of natural or synthetic phytohormones of the auxin and cytokinin classes in a concentration range from 0.01 to 10 mg/l. The culture media are additionally stabilised osmotically with sugar alcohols (for example mannitol) or sugar (for example glucose) or salt ions (for example $CaCl_2$), and are adjusted to a pH in the range from 5.6 to 6.5.

A more detailed description of conventional culture media will be found, for example, in Koblitz, H., Methodische Aspekte der Zellund Gewebezüchtung bei Gramineen unter besonderer Berücksichtigung der Getreide, Kulturpflanze XXII, 1974, 93–157.

A particularly suitable technique of gene transformation is "polyethylene glycol treatment", where the term "polyethylene glycol" within the scope of this invention denotes not only the substance polyethylene glycol itself, but will also be understood as generic term for all substances that likewise modify the protoplast membrane and are employed e.g. in the field of cell fusion. The term thus also comprises other polyhydric alcohols of longer chain length, for example polypropylene glycol (425 to 4000 g/mole), polyvinyl alcohol or polyhydric alcohols whose hydroxyl groups are partially or completely etherified, as well as the detergents which are commonly employed in agriculture and tolerated by plants, and which are described e.g. in the following publications:

"Mc Cutcheon's Detergents and Emulsifiers Annual" MC Publishing Corp., Ridgewood, N.J., 1981;

Stache, H., "Tensid-Taschenbuch", Carl Hanser Verlag, Munich/Vienna, 1981

If polyethylene glycol itself is used (as in Examples 1 to 3, 5 and 7), then it is preferred to use a polyethylene glycol having a molecular weight in the range from 1000 to 10,000 g/mole, preferably from 3000 to 8000 g/mole.

Of the above mentioned substances, it is preferred to use polyethylene glycol itself.

A substantial and reproducible transformation frequency of $10^{-5}$ is achieved by means of the techniques described above. However, this frequency can be greatly improved on by the appropriate techniques described in more detail hereinafter.

In the polyethylene glycol treatment, the procedure can be for example such that either a suspension of the protoplasts is added to a culture medium and then the gene, which is normally employed as plasmid, is added in a mixture of polyethylene glycol and culture medium, or, advantageously, protoplasts and gene (plasmid) are first added to the culture medium and then polyethylene glycol is added. In the process of this invention, electroporation and heat shock treatment have also proved particularly advantageous techniques.

In electroporation [Neumann, E. et al., The EMBO Journal 7, 841–845 (1982)], protoplasts are transferred to an osmoticum, for example a mannitol/magnesium solution and the protoplast suspension is introduced into the electroporator chamber between two electrodes. By discharging a condenser over the suspension, the protoplasts are subjected to an electrical impulse of high voltage and brief duration, thereby effecting polarisation of the protoplast membrane and opening of the pores in the membrane.

In the heat treatment, protoplasts are suspended in an osmoticum, for example a solution of mannitol/calcium chloride, and the suspension is heated in small containers, for example centrifuge tubes, preferably in a water bath. The duration of heating will depend on the chosen temperature. In general, the values are in the range of 40° C. for 1 hour and 80° C. for 1 second. Optimum results are obtained at a temperature of 45° C. over 5 minutes. The suspension is subsequently cooled to room temperature or lower.

It has also been found that the transformation frequency can be increased by inactivating the extracellular nucleases. Such an inactivation can be effected by using divalent cations that are tolerated by plants, for example magnesium or calcium, and also preferably by carrying out the transformation at a high pH value, with the optimum pH range being from 9 to 10.5.

Surprisingly, the selective use of these different methods results in the enormous increase in transformation frequency that has long been an objective in the field of genetic engineering.

The lower the transformation frequency in gene transformation, the more difficult and time-consuming it is to find the few cloned cells resulting from the transformed cells from among the enormous number of non-transformed clones. Where the transformation frequency is low, the use of conventional screening techniques is almost or completely impossible, unless the gene employed is one with selective marker function (e.g. resistance to a specific substance). Low transformation frequency thus requires a very substantial investment in time and effort when using genes without marker function.

In transformations using genes without marker function it is only possible to employ conventional screening techniques for finding cloned cells by selection efficiently and successfully if the transformation frequency is in the order of percentages (about $10^{-2}$). As will be shown below, the desired transformation frequency can now be achieved by means of the process of this invention. Surprisingly, the specific use of different techniques in the process of this invention results in an enormous increase in the previously attained transformation frequency up to 1 to 2%.

Combining foreign gene and receptor protoplasts before employing the other techniques such as polyethylene glycol treatment, electroporation and heat shock treatment brings about an improvement in transformation frequency of the order of about a power of ten as compared with a procedure in which the sequence of the steps employed is different.

Electroporation effects a 5- to 10-fold, and heat shock treatment a 10-fold or greater, improvement in transformation frequency.

A combination of two or three of the following techniques has proved advantageous: polyethylene glycol treatment, heat shock treatment and electroporation, with particularly good results being obtained by employing these techniques after the foreign gene and protoplasts have been introduced into a solution. The preferred technique is heat shock treatment before the polyethylene glycol treatment and the optional subsequent electroporation. In general, the additional electroporation effects a further increase in transformation frequency; but in some cases the results obtained by heat shock and polyethylene glycol treatment are no longer essentially improved by additional electroporation.

Just as the techniques can be combined with one another, so it is also possible to combine the use of divalent cations which are tolerated by plants and/or carrying out the transformation at pH 9 to 10.5 both with individual techniques, as well as combined techniques, preferably with polyethylene glycol treatment, heat shock treatment and electroporation. The numerous combination possibilities permit the process of this invention to be adapted very well to the respective conditions.

The combination of heat shock treatment, polyethylene glycol treatment and, optionally, electroporation subsequent to the already existing combination of foreign gene and receptor protoplasts results in a transformation frequency of $10^{-2}$ to $10^{-3}$.

Accordingly, the process of this invention permits a high transformation frequency to be achieved without utilising biological vectors for the transformation, for example cauliflower mosaic virus or Agrobacterium.

An advantageous method comprises for example transferring protoplasts to a mannitol solution and mixing the protoplast suspension so obtained with the aqueous solution of the gene. The protoplasts are then incubated in this mixture for 5 minutes at 45° C. and subsequently cooled to 0° C. over 10 seconds. Then polyethylene glycol (mol. wt. 3000 to 8000) is added until the concentration is in the range from 1 to 25%, preferably about 8%. After cautious thorough mixing, treatment is carried out in an electroporator. The protoplast suspension is then diluted with culture medium and the protoplasts are taken into culture.

The process of this invention is suitable for the transformation of all plants, especially those of the systematic groups Angiospermae and Gymnospermae.

Among the Gymnospermae, the plants of the Coniferae class are of particular interest.

Among the Angiospermae, plants of particular interest are, in addition to deciduous trees and shrubs, plants of the following families: Solanaceae, Cruciferae, Compositae, Liliaceae, Vitaceae, Chenopodiaceae, Rutaceae, Bromeliaceae, Rubiaceae, Theaceae, Musaceae or Gramineae and of the order Leguminosae, in particular of the family Papilionaceae. Preferred plants are representatives of the Solanaceae, Cruciferae and Gramineae families.

To be particularly mentioned are plants of the species Nicotiana, Petunia, Hyoscyamus, Brassica und Lolium, as for example, *Nicotiana tabacum, Nicotiana plumbagenifolia, Petunia hybrida, Hyoscyamus muticus, Brassica napus, Brassica rapa* and *Lolium multiflorum*.

In the field of transformation of plant cells, interest focuses in particular on the high yield cultivated plants such as maize, rice, wheat, barley, rye, oats and millet.

All plants which can be produced by regeneration from protoplasts can also be transformed utilising the process of this invention. So far it has not been possible to manipulate genetically representatives of the Gramineae family (grasses), which also comprises cereals. It has now been shown that graminaceous cells, including cereal cells, can be transformed genetically by the above described method of direct gene transformation. In the same way, transformation of cultivated plants of the genus Solanum, Nicotiana, Brassica, Beta, Pisum, Phaseolus, Glycine, Helianthus, Allium, wheat, barley, oat, Setaria, rape, rice, Cydonia, Pyrus, Malus, Rubus, Fragaria, Prunus, Arachis, Secale, Panicum, Saccharum, Coffea, Camellia, Musa, Ananas, Vitis or Citrus is possible and desirable, even if the total yields and crop areas are smaller worldwide.

The proof of transformed genes can be adduced in a manner known per se, for example by crossing analyses and molecular biological assays, including in particular the Southern blot analysis and enzyme activity tests.

The Southern blot analysis can be carried out for example as follows: the DNA isolated from the transformed cells or protoplasts is electrophoresed in 1% agarose gel after treatment with restriction enzymes and transferred to a nitrocellulose membrane [Southern, E. M., J. Mol. Biol. 98, 503–517 (1975)], and hybridised with the DNA whose existence it is desired to establish and which was nick-translated [Rigby, W. J., Dieckmann, M., Rhodes, C. and P. Berg, J. Mol. Biol. 113, 237–51, (1977)] (DNA specific activity $5 \times 10^8$ to $10 \times 10^8$ c.p.m./$\mu$g). The filters are washed 3 times for 1 hour with an aqueous solution of 0.03 M sodium citrate and 0.3 M sodium chloride at 65° C. The hybridised DNA is visualised by darkening an X-ray film for 24 to 48 hours.

Testing for enzyme activity—explained in more detail in the assay for aminoglycoside phosphotransferase (enzyme for kanamycin-specific phosphorylation)—can be carried out for example as follows: Callus or leaf pieces (100 to 200 mg) are homogenised in 20 $\mu$l of extraction buffer in an Eppendorf centrifuge tube. The buffer is modified from that used by Herrera-Estrella, L., DeBlock, M., Messens, E., Hernalsteens, J.-P., Van Montagu, M. and J. Schell, EMBO J. 2, 987–995 (1983) omitting bovine serum albumin and adding 0.1 M sucrose. The extracts are centrifuged for 5 minutes at 12000 g and bromophenol blue is added to the supernatant to a final concentration of 0.004%. The proteins in 35 $\mu$l of supernatant are separated by electrophoresis in a 10% non-denaturing polyacrylamide gel. The gel is covered with a layer of agarose gel containing kanamycin and $\gamma$-$^{32}$P labelled ATP, incubated, and the phosphorylated reaction products are transferred to Whatman p81 phosphocellulose paper. The paper is washed 6 times with deionised water at 90° C. and then autoradiographed.

The following Examples illustrate the present invention in more detail but without limiting the scope thereof. They describe the construction of a hybrid gene and the insertion thereof in carrier DNA sequences of cyclic character, the transfer of said hybrid gene into plant cells, selection of the transformed plant cells and regeneration of complete plants from the transformed plant cells as well as the genetic crossing and molecular biological analysis thereof.

In the Examples, the process of the invention is illustrated as follows:

1) by transformation of tobacco plants by transfer of the NPT II gene by joining promoter and termination signals of the CaMV gene VI to the NPT II gene, inserting said gene into the pUC8 plasmid and transferring the resultant chimaeric plasmid into isolated tobacco protoplasts by polyethylene glycol treatment;
2) by transformation of plants of the genus Brassica by transfer of the NPT II gene by joining promoter and termination signals of the CaMV gene VI to the NPT II gene, inserting this construction instead of the CaMV gene VI into the CaMV genome, and transferring the resultant chimaeric plasmid into isolated Brassica protoplasts by polyethylene glycol treatment, and 3) by transformation of plants of the genus Lolium by transfer of the NPT II gene by joining promoter and termination signals of the CaMV gene VI to the NPT II gene, inserting said gene into the pUC8 plasmid, and transferring the resultant chimaeric plasmid into isolated Lolium protoplasts by polyethylene glycol treatment.

Further, the advantageous effect on the transformation by heat shock treatment and electroporation as well as the combined method of heat shock treatment, polyethylene glycol treatment and electroporation after combining protoplasts and NPT II gene will be exemplified.

EXAMPLE 1

Transformation of Cells of Nicotiana tabacum c.v. Petit Havana SRI by Transfer of the NPT II Gene a) Construction of the pABDI Plasmid The freely available plasmids pKm 21 and pKm 244 [Beck, E. et al., Gene 19, 327–336 (1982)] are cut with the PstI restriction endonuclease. The fragments of the plasmids which are used for recombination are purified by electrophoresis in 0.8% agarose gel. The plasmid pKm 21244 resulting from the combination of the fragments contains a combination of the 5'- and 3'-Bal 31 deletions of the NPT II gene, as described by Beck et al in Gene 19, 327–336 (1982). Joining the promoter signal of cauliflower mosaic virus to the HindIII fragment of the plasmid pKm 21244 is effected by constructing the linker plasmid pJPAX. The coupling plasmid pJPAX is obtained from the plasmids pUC8 and pUC9 [Messing, J. and J. Vieira, Gene 119, 269–276 (1982)]. 10 base pairs of the linker sequence of the plasmid pUC9 are deleted by restriction at the HindIII and SalI sites and the resultant cohesive ends are filled in by treatment with the polymerase I Klenow fragment [Jacobson, H. et al., Eur. J. Biochem. 45, 623, (1974)] and ligating the polynucleotide chain, thus restoring the HindIII site. An 8 base pair synthetic XhoI linker is inserted at the SmaI site of this deleted linker sequence. Recombination of the appropriate XorI and HindIII fragments of the plasmid pUC8 and of the modified plasmid pUC9 yields the plasmid pJPAX with a partially asymmetric linker sequence containing the following sequence of restriction sites: EcoRI, SMaI, BamHI, SalI, PstI, HindIII, BamHI, XhoI and EcoRI. Joining of the 5' expression signals of the CaMV gene VI and the HindIII fragment of the NPT II gene is carried out on the plasmid pJPAX by inserting the promoter region of the CaMV VI gene between the PstI and HindIII sites. The plasmid so obtained is restricted at its single HindIII site and the HindIII fragment of the plasmid pKm 21244 is inserted into this restriction site in both orientations, yielding the plasmids pJPAX CaKm⁺ and pJPAX CaKm⁻. To provide an EcoRV site near the 3'-terminal region of the NPT II hybrid gene, a BamHI fragment of the plasmid pJPAX CaKm⁺ is inserted into the BamHI site of the plasmid pBR 327 [Soberon, X. et al., Gene 9, 287–305 (1980)], yielding the plasmid pBR 327 CaKm. The EcoRV fragment of the plasmid pBR 327 CaKm, which contains the new DNA construction, is used to replace the EcoRV region of the CaMV gene VI, which is cloned at the SalI site in the plasmid pUC8, thereby placing the protein-coding DNA sequence of the NPT II gene under the control of the 5' and 3' expression signals of the cauliflower mosaic gene VI. The plasmids so obtained are designated pABDI and pABDII respectively (q.v. FIG. 1).

b) Transformation of Protoplasts of Nicotiana tabacum c.v. Petit Havana SRI by Transfer of the NPT Gene as Part of the Plasmid pABDI by PEG Treatment Tobacco protoplasts at a population density of 2·10⁶ per ml are suspended in 1 ml of K₃ medium [q.v. Z. Pflanzenphysiologie 78, 453–455 (1976); Mutation Research 81 (1981) 165–175], containing 0.1 mg/l of 2,4-dichlorophenoxyacetic acid, 1.0 mg/l of 1-naphthylacetic acid and 0.2 mg/A of 6-benzylaminopurine, which protoplasts have been obtained beforehand from an enzyme suspension by flotation on 0.6 molar sucrose at pH 5.8 and subsequent sedimentation (100 g for 5 minutes) in 0.17 M calcium chloride at pH 5.8. To this suspension are added, in succession, 0.5 ml of 40% polyethylene glycol (PEG) with a molecular weight of 6000 in modified (adjusted again to pH 5.8 after autoclaving) F-medium [Nature 296, 72–74 (1982)] and 65 $\mu$l of an aqueous solution containing 15 $\mu$g of the plasmid pABDI and 50 $\mu$g of calf thymus DNA. This mixture is cultured for 30 minutes at 26° C. with occasional agitation and subsequent stepwise dilution with F medium. The protoplasts are isolated by centrifuging (5 minutes at 100 g) and resuspended in 30 ml of fresh K₃ medium. Further incubation is carried out in 10 ml portions in Petri dishes of 10 cm diameter at 24° C. and in the dark. The population density is 6.3·10⁴ protoplasts per ml. After 3 days the culture medium in each dish is diluted with 0.3 parts by volume of fresh K₃ medium and incubated for a further 4 days at 24° C. and 3000 lux. After a total of 7 days, the clones developed from the protoplasts are embedded in a culture medium solidified with 1% of agarose and containing 50 mg/l, of kanamycin, and cultured at 24° C. in the dark by the bead type culture method [Plant Cell Reports, 2, 244–247 (1983)]. The culture medium is replaced every 5 days by fresh nutrient solution of the same kind.

c) Regeneration of Kanamycin-Resistant Tobacco Plants

After 3 to 4 weeks of continued culturing in kanamycin-containing culture medium, the resistant calli of 2 to 3 mm diameter are transferred to agar-solidified LS culture medium [Physiol. Plant 18, 100–127 (1965)], containing 0.05 mg/l of 2,4-dichlorophenoxyacetic acid, 2 mg/l of 1-naphthylacetic acid, 0.1 mg/l of 6-benzylaminopurine, 0.1 mg/l of kinetin and 75 mg/l of kanamycin. Kanamycin-resistant Nicotiana tabacum Petit Havana SRI plants are obtained by inducing shoots on LS medium containing 150 mg/l of kanamycin and 0.2 mg/l of 6-benzylaminopurine, and subsequent rooting on T medium [Science 163, 85–87 (1969)].

d) Detection of the NPT II Gene in Hereditary Material of Plants

Samples of 0.5 g of callus of the transformed cell cultures or leaf tissue of the plants regenerated therefrom are homogenised at 0° C. in 15% saccharose solution containing 50 mmol/l of 1-ethylenediamine N,N,N',N'-tetraacetic acid (EDTA), 0.25 mol/l of sodium chloride and 50 mmol/l of $\alpha,\alpha,\alpha$-tris(hydroxymethyl)methylamine hydrochloride (TRIS-HCl) at pH 8. Centrifugation of the homogenate for 5 minutes at 1000 g gives a crude nuclear pellet which is resuspended at pH 8.0 in 15% saccharose solution containing 50 mmol/l of EDTA and 50 mmol/l of TRIS-HCl. Sodium dodecyl sulfate is added to a final concentration of 0.2% and heated for 10 minutes to 70° C. After cooling to 20°–25° C., potasasium acetate is added to the mixture to a concentration of 0.5 mol/l This mixture is incubated for 1 hour at 0° C. The precipitate is centrifuged for 15 minutes at 4° C. in a microcentrifuge. The DNA is precipitated from the supernatant with 2.5 volumes of ethanol at 20°–25° C. The isolated DNA is dissolved in a solution of 10 mmol of TRIS-HCl containing 10 $\mu$g/ml of ribonuclease A. After incubation for 10 minutes at 37° C., proteinase K is added to a concentration of 250 250 $\mu$g/ml and incubation is continued for 1 hour at 37° C. The proteinase K is removed by phenol and chloroform/isoamyl alcohol extractions. The DNA is precipitated from the aqueous phase by addition of 0.6 part by volume of a 0.6 molar solution of sodium acetate in isopropanol and dissolved in 50 μl of a solution containing 10 mmol/l of TRIS-HCl and 5 mmol/l of EDTA at pH 7.5. This preparation yields DNA sequences which contain substantially more than 50,000 base pairs. Restriction of this DNA with EcoRV endonuclease, hybridisation of the fragments with radioactively labelled HindIII fragments of the NPT II gene and comparison with the plasmid pABDI show, in Southern blot analysis, the presence of the NPT II gene in the cell nucleus DNA of the transformed Nicotiana tabacum cells.

e) Evidence of the Transfer of the Transformed Gene to Sexual Offspring and of its Heredity as Normal Plant Gene Extensive genetic crossing analyses and detailed molecular biological studies (for example Southern blot analysis of the DNA of the plant genome; investigation of the enzyme activity of the aminoglycoside phosphotransferase, i.e. the enzyme for the kanamycin-specific phosphorylation) with the genetically transformed plants (first generation and progeny) have yielded the following results:
1. the baceterial gene is stably integrated into the plant genome;
2. it is normally unchanged and regularly transferred to crossed progeny;
3. its heredity corresponds to that of a natural, simple dominant plant gene;
4. the molecular analysis by DNA hybridisation and enzyme test confirms the results of the genetic crossing analysis;
5. the genetically transformed plants retain their normal, natural phenotype during the treatment, i.e. no undesirable modifications are observed.

These results show that the process of this invention for the direct transfer of a gene into protoplasts affords the best mode of specifically transforming plant material genetically. The genetic transformation is stable and unwanted modifications in the genotype of the plant do not occur. Parallel results are also obtained when carrying out the transformation described in the foregoing Example with *Nicotiana plumbagenifolia, Petunia hybrida, Hyoscyamus muticus* and *Brassica napus*.

EXAMPLE 2

Figure 2:
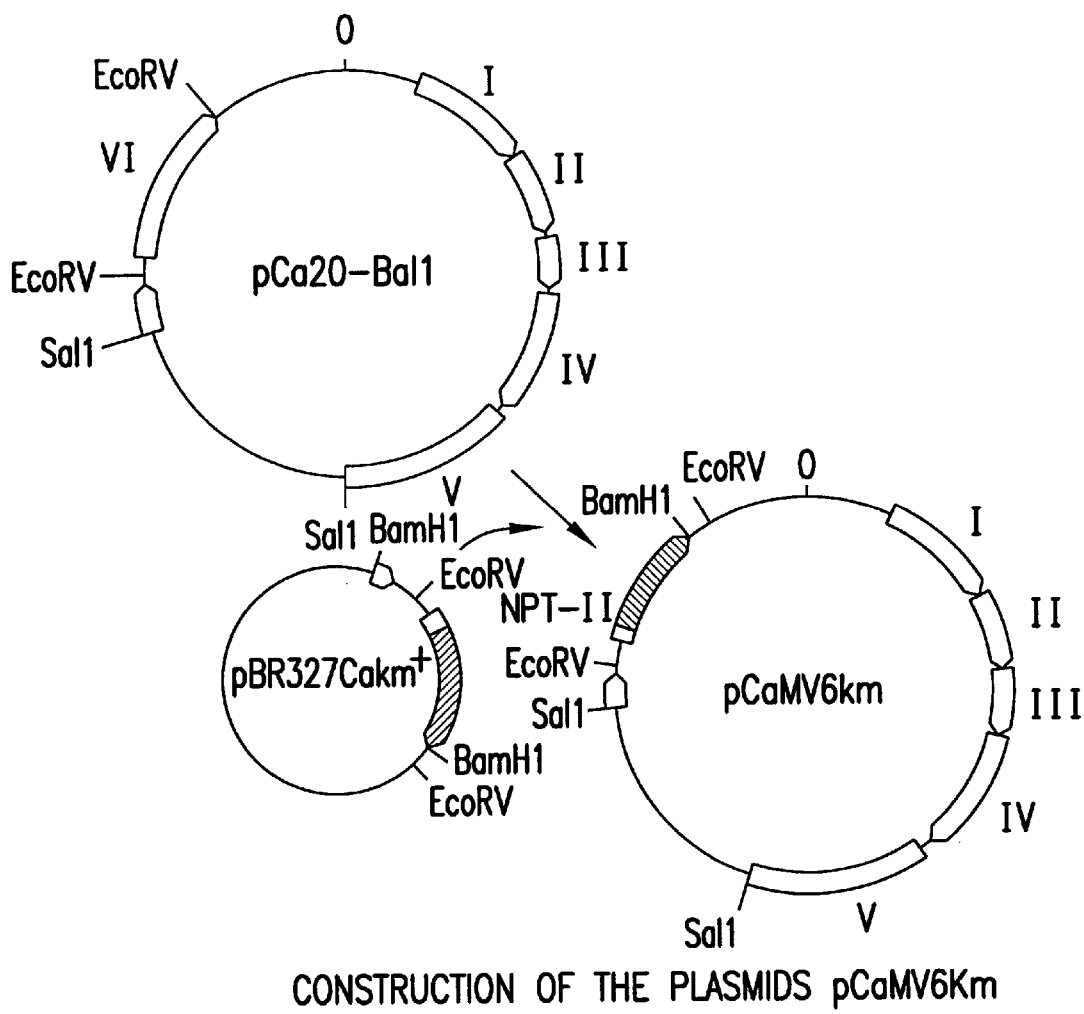
FIG. 2 depicts the construction of the pCaMV6Km plasmid.

Transformation of Cells of *Brassica rapa* c.v. Just Right by Transfer of the NPT II Gene a) Construction of the Plasmid pCaMV6Km The plasmid pBR 327 CaKm$^+$ described in Example 1a is digested with restriction endonuclease EcoRV and the EcoRV restriction fragment containing the kanamycin-resistant gene (NPT II) is used to replace the EcoRV fragment of the plasmid pCa20-Bal I, which fragment contains the gene VI of cauliflower mosaic virus, yielding the plasmid pCaMV6Km (FIG. 2). The plasmid Ca20-Bal I is a chimaeric CaMV plasmid which is derived from the natural deletion mutant CN4-184. The entire region II is missing from this plasmid, except for the first 5 codons and the translation stop signal TGA. An XhoI coupling component was inserted immediately before the stop codon in region II.

b) Transformation of Protoplasts of *Brassica rapa* c.v. Just Right by Transfer of the NPT Gene as Part of the Plasmid pCaMV6Km by PEG Treatment

*Brassica rapa* protoplasts are washed with a suitable osmoticum and suspended in a population density of $5 \cdot 10^6$ per ml in a culture medium prepared according to Protoplasts 83, Proceedings Experientia Supplementum, Birkhauser Verlag, Basel, Vol. 45 (1983), 44–45. 40% polyethylene glycol (PEG) with a molecular weight of 6000, dissolved in modified F medium (pH 5.8) (q.v. Example 1b), is mixed with the protoplast suspension to a final concentration of 13% PEG. To this mixture is added immediately a solution of 10 μg of plasmid pCaMV6Km digested with endonuclease SalI, and 50 μg of calf thymus DNA in 60 μg of water. With occasional agitation, the mixture is incubated for 30 minutes at 20°–25° C. Then 3×2 ml of modified F medium (6 ml in all) and 2×2 ml of culture medium (4 ml in all) are added at 5 minute intervals. The protoplast suspension is transferred to 10 cm Petri dishes and made up to a total volume of 20 ml with additional culture medium. These protoplast suspensions are incubated in the dark for 45 minutes at 26° C. The protoplasts are isolated by sedimentation for 5 minutes at 100 g, taken up in an initially liquid and then solidifying agarose gel culture medium and cultured by the bead type culture method [Plant Cell Reports 2, 244–247 (1983)]. After 4 days, in the development stage of the first cell division, kanamycin is added to the cultures in a concentration of 50 mg/l. The liquid culture medium surrounding the agarose segments is replaced every 4 days by fresh kanamycin-containing nutrient solution. After 4 weeks the kanamycin-resistant clones are isolated and then further cultured by providing them weekly with kanamycin-containing nutrient solution (50 mg/l).

c) Detection of the NPT II Gene in the Hereditary Material of the Plants

The presence of the NPT II gene in the cell nucleus of the transformed *Brassica rapa* cells can be detected by isolation of the cell nucleus DNA and restriction thereof and hybridisation of the DNA fragments as described in Example 1 d).

EXAMPLE 3

Transformation of Protoplasts of Graminaceous Plants of the Species *Lolium multiflorum*

Protoplasts of *Lolium multiflorum* (Italian ryegrass) are taken up at a concentration of $2 \cdot 10^6$ per ml in 1 ml of 0.4 molar mannitol at pH 5.8. To this suspension are added, in succession, 0.5 ml of 40% polyethylene glycol (PEG) with a molecular weight of 6000 in modified (pH 5.8) F medium [Nature 296, 72–74 (1982)], and 65 μl of an aqueous solution containing 15 μg of the plasmid pABDI and 50 μg of calf thymus DNA. This mixture is incubated for 30 minutes at 26° C. with occasional agitation and subsequently diluted with F medium, as described in Nature 296 (1982), 72–74. The protoplasts are isolated by centrifugation (5 minutes at 100 g) and taken up in 4 ml of CC culture medium [Potrykus, Harms, Lörz, Callus formation from cell culture protoplasts of corn (Zea Mays L.), Theor. Appl. Genet. 54, 209–214 (1979)] and incubated in the dark at 24° C. After 14 days the developing cell cultures are transferred to the same culture medium, but with the antibiotic G-418 (commercially available; GIBCO EUROPE Product Catalogue, Catalogue No. 0661811). G-418 is toxic to Lolium cells at a concentration of 25 mg/l and permits solely the further development of cells which have taken up the bacterial gene for kanamycin resistance. G-418 is a kanamycin analog with substantially better activity in graminaceous cells than kanamycin itself. Resistant cell colonies are transferred to agar medium (the same medium as above, 25 ml/l G-418, without osmoticum) and, after reaching a size of several grams fresh weight per cell colony, analysed for the presence of the bacterial gene and for the biological activity of the gene. The former analysis is made by hybridisation of a radioactively labelled DNA sample of the gene with DNA which has been isolated from the cell culture; while the latter is made by detecting the enzyme activity by phosphorylation of kanamycin with radioactive ATP. Both molecular analyses yielded unequivocal proof of the genetic transformation of the cell colonies which had been selected on G-418. The assays constitute the first proof of the genetic transformation of protoplasts of graminaceous plants and furthermore prove that, in principle, protoplasts of grasses can be genetically manipulated by the described process. The possibility of genetically manipulating cultivated grasses, for example cererals, is thus also afforded.

EXAMPLE 4

Transformation of Cell Culture Cells of Nicotiana tabacum by Transferring the NPT Gene by Means of Electroporation Protoplasts are produced by sedimentation from 50 ml of a log phase suspension culture of the nitrate reductase deficiency variant of Nicotiana tabacum, cell strain nia-115 [Müller, A. J. and R. Grafe, Mol. Gen. Genet. 161, 67–76 (1978)], and resuspended in 20 ml of enzyme solution [2% Cellulase Onozuka R-10, 1% Mazerozym R-10 and 0.5% Driselase (available from Chemische Fabrik Schweizerhalle, Basel) in a wash solution (0.3 M mannitol, 0.04 M calcium chloride and 0.5% 2-(N-morpholino) ethanesulfonic acid), adjusted to pH 5.6 with KOH] and incubated for 3 hours on a gyratory shaker at 24° C. The protoplasts are then separated from undigested tissue by filtering them through a 100 $\mu$m mesh sieve. An equal volume of 0.6 M sucrose is added and the suspension is centrifuged for 10 minutes at 100 g. The protoplasts floating on the surface are collected and washed 3 times by sedimentation in the wash solution.

Transformation is carried out by electroporation. The chamber of a Dialog® "Porator" (available from Dialog GmbH, Harffstr. 34, 4000 Düsseldorf, West Germany) is sterilised by washing with 70% ethanol and then 100% ethanol and dried by a current of sterile air from a ventilator with laminary air flow). The protoplasts are suspended at a concentration of $1\times10^6$/ml in 0.4 M mannitol solution, adjusted with magnesium chloride to a resistance of 1.4 kOhm and pABDI DNA is added in a concentration of 10 $\mu$g/ml. 0.38 ml samples of this protoplast suspension are subjected 3 times at 10 second intervals to a charge of 1000 volts or to a charge, of 2000 volts. The protoplasts are then cultured in a concentration of $1\times10^5$/ml in 3 ml of AA-CH medium [AA medium of Glimelius, K. et al., Physiol. Plant. 44, 273–277 (1978)], modified by increasing the inositol concentration to 100 mg/l and the saccharose concentration to 34 g/l, as well as by adding 0.05 ml/l of 2-(3-methyl-2-butenyl)adenine, and which is solidified by a 0.6% content of agarose (Sea Plaque, FMC Corp., Marine Colloids Division, P.O. Box 308, Rockland, Me. 04841, USA). After 1 week, the agarose layer containing the protoplasts is transferred to 30 ml of liquid AA-CH medium which contains 50 mg/l of kanamycin. After 3 weeks, during which time half the liquid medium is replaced weekly by fresh medium of the same composition, the transformed cell colonies can be observed visually. Four weeks after being transferred to the medium containing kanamycin, these cell colonies are transferred to AA medium (Glimelius, K. et al., Physiol. Plant. 44, 273–277 (1978); 0.8% agar), which contains 50 mg/l of kanamycin, for further culturing and investigation. Confirmation of the successful transformation is by DNA hybridisation and testing for the enzyme activity of aminoglycoside phosphotransferase.

Analogous assays with protoplasts of Brassica rapa and Lolium multiflorum also result in successful transformations.

EXAMPLE 5

Transformation of Cells of Nicotiana tabacum by Transfer of the NPT II Gene by Electroporation The preparation of the electroporator is as described in Example 4 and of the protoplasts as in Example 1.

For transformation, protoplasts of Nicotiana tabacum are resuspended in a concentration of $1.6\times10^6$/ml in mannitol solution (0.4 M, buffered with 0.5% w/v of 2-(N-morpholino)ethanesulfonic acid; pH pH 5.6). The resistance of the protoplast suspension is measured in the porator chamber (0.38 ml) and adjusted to 1 to 1.2 kOhm with magnesium chloride solution (0.3 M). 0.5 ml samples are put into capped plastic tubes (5 ml volume) to each of which are added initially 40 $\mu$l of water containing 8 $\mu$g of pABDI (linearised with SmaI) and 20 $\mu$g of calf thymus DNA, and then 0.25 ml of polyethylene glycol solution (24% w/v in 0.4 M mannitol). Nine minutes after addition of the DNA, 0.38 ml portions are put into the pulse chamber and 10 minutes after the addition of DNA, the protoplast suspensions present in the chamber are subjected to 3 impulses (1000–2000 volts) at 10 second intervals. The treated portions are put into Petri dishes of 6 cm diameter and kept for 10 minutes at 20° C. Then 3 ml of $K_3$ medium containing 0.7% w/v of Sea Plaque agarose are added to each Petri dish and the contents of the dish are thoroughly mixed. After solidification of the contents of each dish, the cultures are kept for 1 day at 24° C. in the dark and then for 6 days in light. The protoplast-containing agarose is then cut into quarters and introduced into liquid medium. The protoplasts are then cultured by the bead type culturing method. Callus tissues which are obtained by selection of the transformed material with kanamycin and plants regenerated therefrom contain the NPT II enzyme (aminoglycoside phosphotransferase) as product of the NPT II gene.

Electroporation induces a 5- to 10-fold increase in the frequency of transformation compared with the method without electroporation. Analogous assays with Brassica rapa c.v. Just Right and Lolium multiflorum also bring about an increase in the frequency of transformation of the same order of magnitude.

EXAMPLE 6

Transformation of Cells of Nicotiana tabacum by Transfer of the NPT II Gene by Means of Heat Shock Protoplasts isolated from leaves or cell cultures of Nicotiana tabacum are isolated as described in Examples 1 and 4 and transferred to an osmotic medium as described in the preceding Examples. The protoplast suspensions are kept for 5 minutes at 45° C., cooled with ice for 10 seconds and then the plasmid pABDI is added as described in Examples 1 and 4. The heat shock treatment increases the transformation frequency by a factor of 10 or higher compared with a transformation carried out without this treatment.

Analogous assays with the protoplasts and plasmids described in Examples 2 and 3 also bring about an increase in the frequency of transformation of the same order of magnitude.

EXAMPLE 7

Transformation of Different Plant Cells by Transfer of the NPT II Gene by Combining Protoplasts and Gene as First Step and Subsequent Combined Treatment Protoplasts of the plants:
Nicotiana tabacum c.v. Petit Havana SRI (A),

*Brassica rapa* c.v. Just Right (B) and
*Lolium multiflorum* (C)
are isolated and transferred to an osmotic medium as described in Example 5. The protoplast suspensions of A) and C) are mixed with the plasmid pABDI (Example 1a), and those of B) with the plasmid pCaMV6Km (Example 2a) as described in Examples 1 to 3, but without simultaneous treatment with polyethylene glycol. The protoplast suspensions are then subjected to a heat shock treatment as described in Example 6, then to a polyethylene glycol treatment as described in Examples 1 to 3, and finally subjected to electroporation as described in Example 5. The transformation frequency in this procedure is in the range from $10^{-3}$ to $10^{-2}$, but may be from 1 to 2% depending on the conditions. (The transformation frequency in Examples 1 to 3 is in the order of about $10^{-5}$). Results in the range from $10^{-3}$ to $10^{-2}$ are also obtained if, after combining protoplasts and plasmids, the subsequent steps of heat shock, polyethylene glycol treatment and electroporation are employed in different sequence.

What is claimed is:

1. A transgenic Brassica cell comprising foreign DNA unaccompanied by T-DNA border regions of a Ti plasmid, said foreign DNA being under the control of plant expression signals and integrated into the plant hereditary material, such that said foreign DNA is transmissible to the progeny of a plant regenerated from said transgenic plant cell, wherein said transgenic plant cell is transformed by a process for the stable integration of said foreign DNA comprising:

contacting said foreign DNA directly with a plant protoplast in a medium under conditions that render the plant protoplast membrane permeable to DNA molecules until said foreign DNA has been taken up by the protoplast, wherein said stable integration is carried out by a technique selected from the group consisting of polyethylene glycol treatment, electroporation, heat shock treatment, and combinations thereof.

2. A transgenic Brassica plant cell according to claim 1 wherein the plant cell is selected from the group consisting of *Brassica napus* and *Brassica rapa* plant cells.

3. A transformed living Brassica protoplast or plant cell, derived from the transgenic Brassica plant cell of claim 1, each comprising said foreign DNA.

4. A transformed living Brassica protoplast, cell, tissue or whole plant, derived from the transgenic Brassica cell of claim 1, each comprising said foreign DNA.

5. A transgenic Brassica plant derived from the Brassica cell of claim 1, said Brassica plant comprising said foreign DNA.

6. The transgenic Brassica plant of claim 5, wherein said foreign DNA comprises a structural gene flanked by plant expression signals.

7. The transgenic Brassica plant of claim 5, wherein said foreign DNA comprises a gene whose structural part is of plant, animal, microbial, viral or synthetic origin and whose expression signals are of plant, animal or synthetic origin.

8. The transgenic Brassica plant of claim 5, wherein said Brassica is selected from the group consisting of *Brassica napus* and *Brassica rapa*.

9. The transgenic Brassica plant of claim 6, wherein said Brassica is selected from the group consisting of *Brassica napus* and *Brassica rapa*.

10. The transgenic Brassica plant of claim 7, wherein said Brassica is selected from the group consisting of *Brassica napus* and *Brassica rapa*.

\* \* \* \* \*